US007632859B2

(12) United States Patent
Li et al.

(10) Patent No.: US 7,632,859 B2
(45) Date of Patent: Dec. 15, 2009

(54) IONTOPHORETIC DELIVERY OF ROTIGOTINE FOR THE TREATMENT OF PARKINSON'S DISEASE

(75) Inventors: Gai Ling Li, Middlesex (GB); Johanna Aaltje Bouwstra, Barendrecht (NL); Hans-Michael Wolff, Monheim (DE); Akhmad Karis Nugroho, Leiden (NL)

(73) Assignee: Schwarz Pharma AG, Monheim (DE)

( * ) Notice: Subject to any disclaimer, the term of this patent is extended or adjusted under 35 U.S.C. 154(b) by 797 days.

(21) Appl. No.: 10/713,424

(22) Filed: Nov. 17, 2003

(65) Prior Publication Data

US 2004/0116537 A1 Jun. 17, 2004

(30) Foreign Application Priority Data

Dec. 2, 2002 (EP) .................. 02026871

(51) Int. Cl.
*A01N 43/06* (2006.01)
*A61K 31/38* (2006.01)
*A61N 1/30* (2006.01)

(52) U.S. Cl. .................. 514/438; 514/443; 604/20
(58) Field of Classification Search .................. 514/438
See application file for complete search history.

(56) References Cited

U.S. PATENT DOCUMENTS

| 4,801,586 A | 1/1989 | Minaskanian et al. ........ 514/212 |
| 4,808,414 A | 2/1989 | Peck et al. .................. 424/449 |
| 4,847,253 A | 7/1989 | Buonamici et al. .......... 514/253 |
| 4,915,950 A | 4/1990 | Miranda et al. ............. 424/448 |
| 4,917,896 A | 4/1990 | Peck et al. .................. 424/449 |
| 4,973,468 A | 11/1990 | Chiang et al. ............... 424/449 |
| 4,996,226 A | 2/1991 | Horn |
| 5,034,386 A | 7/1991 | Peck et al. .................. 514/212 |
| 5,043,441 A | 8/1991 | Peck et al. .................. 540/526 |
| 5,069,909 A | 12/1991 | Sharma et al. ............... 424/449 |
| 5,071,645 A | 12/1991 | Johnson et al. ............. 424/486 |
| 5,071,875 A | 12/1991 | Horn et al. .................. 514/613 |
| 5,073,544 A | 12/1991 | Peck et al. .................... 514/24 |
| 5,091,186 A | 2/1992 | Miranda et al. ............. 424/448 |
| 5,108,991 A | 4/1992 | Rajadhyaksha .............. 514/29 |
| 5,118,845 A | 6/1992 | Peck et al. .................. 564/215 |
| 5,124,157 A | 6/1992 | Colley et al. ............... 424/448 |
| 5,142,044 A | 8/1992 | Minaskanian et al. ........ 540/529 |
| 5,147,916 A | 9/1992 | Sweet ........................ 524/266 |
| 5,151,446 A | 9/1992 | Horn et al. .................. 514/617 |
| 5,204,339 A | 4/1993 | Minaskanian et al. ........ 514/182 |
| 5,225,198 A | 7/1993 | Sharma et al. ............... 424/443 |
| 5,234,690 A | 8/1993 | Chiang et al. ............... 424/448 |
| 5,234,945 A | 8/1993 | Belluzzi .................... 514/438 |
| 5,246,997 A | 9/1993 | Sweet ........................ 524/266 |
| 5,252,334 A | 10/1993 | Chiang et al. ............... 424/448 |
| 5,252,335 A | 10/1993 | Chiang ...................... 424/449 |
| 5,271,940 A | 12/1993 | Cleary et al. ............... 424/448 |
| 5,273,755 A | 12/1993 | Venkatraman et al. ...... 424/448 |
| 5,273,756 A | 12/1993 | Fallon et al. ................ 424/448 |
| 5,273,757 A | 12/1993 | Jaeger et al. ................ 424/448 |
| 5,308,625 A | 5/1994 | Wong et al. ................. 424/449 |
| 5,382,596 A | 1/1995 | Sleevi et al. ................ 514/459 |
| 5,393,529 A | 2/1995 | Hoffmann et al. ........... 424/445 |
| 5,456,745 A | 10/1995 | Roreger et al. ............. 106/128 |
| 5,472,946 A | 12/1995 | Peck et al. .................... 514/29 |
| 5,519,034 A | 5/1996 | Kozlik et al. ................ 514/307 |
| 5,532,278 A | 7/1996 | Aberg et al. ................ 514/617 |
| 5,554,381 A | 9/1996 | Roos et al. .................. 424/449 |
| 5,601,839 A | 2/1997 | Quan et al. .................. 424/448 |
| 5,670,164 A | 9/1997 | Meconi et al. ............. 424/448 |
| 5,670,501 A | 9/1997 | Peck et al. ............... 514/234.2 |
| 5,677,346 A | 10/1997 | Aberg et al. .................. 51/617 |
| 5,688,524 A | 11/1997 | Hsu et al. ................... 424/449 |
| 5,733,571 A | 3/1998 | Sackler ....................... 424/449 |
| 5,771,890 A | 6/1998 | Tamada ...................... 128/635 |
| 5,807,570 A | 9/1998 | Chen et al. .................. 424/449 |
| 5,834,010 A | 11/1998 | Quan et al. .................. 424/448 |
| 5,840,336 A | 11/1998 | Hsu et al. ................... 424/484 |
| 5,876,746 A | 3/1999 | Jona et al. ................... 424/449 |
| 5,879,701 A | 3/1999 | Aduett et al. ............... 424/448 |
| 5,891,461 A | 4/1999 | Jona et al. ................... 424/449 |
| 5,902,603 A | 5/1999 | Chen et al. .................. 424/449 |
| 5,906,830 A | 5/1999 | Farinas et al. ............... 424/448 |

(Continued)

FOREIGN PATENT DOCUMENTS

| AU | 746856 | 10/1999 |
| CA | 2532804 | 2/2005 |
| CA | 2532859 | 2/2005 |
| CA | 2547820 | 6/2005 |
| CA | 2546797 | 7/2005 |

(Continued)

OTHER PUBLICATIONS

Panchagnula et al. Transdermal iontophoresis revisted. Curr Op Chem Biol., 2000, 4:468-473.*
Van der Geest, Ronald, et al., "Iontophoretic Delivery of Apomorphine: In Vitro Optimization and Validation". Pharm. Res., vol. 14, 1797-1802, 1997.
Li, G., et al., "Optimization of Transdermal Iontophoretic Delivery of Apomorphine for the Treatment of Parkinson's Disease In Vitro". Proceed. Int'l Symp. Control. Rel. Bioact. Mater., vol. 27, No. 7435, 2000.

(Continued)

*Primary Examiner*—Sreeni Padmanabhan
*Assistant Examiner*—Renee Claytor
(74) *Attorney, Agent, or Firm*—Harness, Dickey & Pierce, P.L.C.

(57) ABSTRACT

By using a composition comprising rotigotine and at least one chloride salt in a concentration of 1 to 140 mmol/l, the composition having a pH of 4 to 6.5 in a iontophoretic device for the treatment of Parkinson's disease, it became possible to obtain a rotigotine flux across the human stratum corneum which was higher than the one previously obtained with conventional passive diffusion systems.

12 Claims, No Drawings

U.S. PATENT DOCUMENTS

| | | | |
|---|---|---|---|
| 5,962,013 A | 10/1999 | Wong et al. | 424/448 |
| 5,980,932 A | 11/1999 | Chiang et al. | 424/448 |
| 5,981,524 A | 11/1999 | Peck et al. | 514/234.2 |
| 6,010,716 A | 1/2000 | Saunal et al. | 424/449 |
| 6,024,974 A | 2/2000 | Li | 424/448 |
| 6,024,976 A | 2/2000 | Miranda et al. | 424/449 |
| 6,057,371 A | 5/2000 | Glennon | 514/649 |
| 6,063,398 A | 5/2000 | Gueret | 424/443 |
| 6,086,905 A | 7/2000 | Peck et al. | 424/406 |
| 6,218,421 B1 | 4/2001 | King | 514/421 |
| 6,221,627 B1 | 4/2001 | Sathe et al. | 435/69.1 |
| 6,242,572 B1 | 6/2001 | Tsui et al. | 530/350 |
| 6,299,900 B1 | 10/2001 | Reed et al. | 424/449 |
| 6,300,365 B1 | 10/2001 | Holman | 514/418 |
| 6,316,022 B1 | 11/2001 | Mantelle et al. | 424/448 |
| 6,344,342 B1 | 2/2002 | Tsui et al. | 435/69.1 |
| 6,393,318 B1 | 5/2002 | Conn et al. | 604/20 |
| 6,398,562 B1 | 6/2002 | Butler et al. | 439/91 |
| 6,416,503 B1 * | 7/2002 | Suzuki et al. | 604/501 |
| 6,465,004 B1 | 10/2002 | Rossi-Montero et al. | 424/448 |
| 6,514,530 B2 | 2/2003 | Skluzacek et al. | 424/468 |
| 6,620,429 B1 | 9/2003 | Müller | 424/449 |
| 6,685,959 B1 | 2/2004 | Moreau et al. | 424/449 |
| 6,687,522 B2 | 2/2004 | Tamada | 600/347 |
| 6,699,498 B1 | 3/2004 | Müller | 424/449 |
| 6,884,434 B1 * | 4/2005 | Muller et al. | 424/487 |
| 6,899,894 B1 | 5/2005 | Klein et al. | 424/448 |
| 7,038,085 B2 | 5/2006 | Rariy et al. | 564/165 |
| 2001/0053777 A1 | 12/2001 | Brecht | |
| 2002/0010201 A1 | 1/2002 | Brecht | 514/388 |
| 2002/0110585 A1 | 8/2002 | Godbey et al. | 424/449 |
| 2003/0027793 A1 * | 2/2003 | Lauterback et al. | 514/63 |
| 2003/0166709 A1 | 9/2003 | Rimpler et al. | |
| 2004/0057985 A1 | 3/2004 | Bracht | 424/449 |
| 2004/0081683 A1 | 4/2004 | Schact et al. | 424/449 |
| 2004/0110673 A1 | 6/2004 | Steinkasserer et al. | 514/12 |
| 2004/0137045 A1 | 7/2004 | Breitenbach et al. | 424/449 |
| 2004/0142904 A1 | 7/2004 | Rariy et al. | 514/63 |
| 2005/0032873 A1 | 2/2005 | Hatzenbuhler et al. | 514/414 |
| 2005/0033065 A1 | 2/2005 | Mueller et al. | 549/74 |
| 2005/0079206 A1 | 4/2005 | Schacht et al. | 424/449 |
| 2005/0107397 A1 | 5/2005 | Galambos et al. | 514/255.03 |
| 2005/0136101 A1 | 6/2005 | Berthold | 424/448 |
| 2005/0175678 A1 | 8/2005 | Breitenbach | 424/448 |
| 2005/0175680 A1 | 8/2005 | Morgan et al. | 424/449 |
| 2005/0182090 A1 | 8/2005 | Mierau et al. | 514/304 |
| 2005/0197385 A1 | 9/2005 | Scheller et al. | 514/438 |
| 2006/0222691 A1 | 10/2006 | Cantor et al. | 424/448 |

FOREIGN PATENT DOCUMENTS

| | | |
|---|---|---|
| CA | 2568850 | 2/2006 |
| DE | 4325855 | 2/1995 |
| WO | WO 93/07842 | 4/1993 |
| WO | WO93/14727 | 8/1993 |
| WO | WO93/16073 | 8/1993 |
| WO | WO 94/04109 | 3/1994 |
| WO | WO 94/07468 | 4/1994 |
| WO | WO94/21244 | 9/1994 |
| WO | WO94/26703 | 11/1994 |
| WO | WO 95/00122 | 1/1995 |
| WO | WO 95/01767 | 1/1995 |
| WO | WO 95/05137 | 2/1995 |
| WO | WO 95/05138 | 2/1995 |
| WO | WO96/00110 | 1/1996 |
| WO | WO 96/22083 | 7/1996 |
| WO | WO 96/22084 | 7/1996 |
| WO | WO 96/40087 | 12/1996 |
| WO | WO 97/09971 | 3/1997 |
| WO | WO 97/29735 | 8/1997 |
| WO | WO 99/49852 | 10/1999 |
| WO | WO 02/15903 | 2/2002 |
| WO | WO2005/063236 | 7/2005 |
| WO | WO2006/050976 | 3/2006 |

OTHER PUBLICATIONS

Luzardo-Alverez, Asteria, et al., "Iontophoretic Delivery of Ropinirole Hydrochloride: Effect of Current Density and Vehicle Formulation". Pharm. Res., vol. 18, No. 12, pp. 1714-1720, Dec. 2001.

den Daas, Isaak, et al., "Transdermal administration of the dopamine agonist N-0437 and seven ester prodrugs: comparison with oral administration in the 6-OHDA turning model". Naunyn-Schmiedeberg's Arch. Pharmacol., vol. 342, pp. 655-659, 1990.

Danhof, M., et al., "An integrated pharmacokinetic-pharmacodynamic approach to optimization of R-apomorphine delivery in Parkinson's disease". Advanced Drug Delivery Reviews, vol. 33, pp. 253-263, 1998.

Li, G., et al., "Iontophoretic Delivery of Apomorphine In Vitro: Physicochemic Considerations". Pharm. Res., vol. 18, No. 11, pp. 1509-1513, Nov. 2001.

Van der Geest, R., et al., "Validation and testing of a new iontophoretic continuous flow through transport cell". Journal of Controlled Release, vol. 51, pp. 85-91, 1998.

Blindauer (2003) Arch. Neurol. 60(12): 1721-1728.

Hsu et al. (1992) Cygnus Therapeutic Systems Project Report N-0923, 2-19.

Levien et al. (2005) Advances in Pharmacy 3(1): 62-92.

Löschmann et al. (1989) Eur. J. Pharmacol. 166: 373-380.

Pfister (1988) Drug and Cosmetic Ind. (Oct.): 44-52.

Pfister (1989) Pharm. Tech. (Mar.): 126-138.

Pfister and Hsieh (1990) Pharm. Tech. (Sep.): 132-140.

Pfister and Hsieh (1990) Pharm. Tech. (Oct.): 54-60.

Pfister et al. (1991) Chemistry in Britain (Jan.): 43-46.

Pfister et al. (1992) Pharm. Tech. (Jan.): 42-58 and 83.

Roy et al. (1996) J. Pharn. Science 85(5): 491-495.

Thomas et al. (1991) STP Pharma Sci 1(1): 38-46.

Nugroho, et. al. (2005) *Transdermal Iontophoretic Delivery of Dopamine Agonists: In Vitro-In Vivo Correlation Based on Novel Compartmental Modeling* (Doctoral thesis, Leiden University), Chapter 3, pp. 37-53.

Alekov et al. (2000) J. Physiology 529(3), 533-539.

Chiang et al. (1995) Controlled Release Society, Inc., pp. 710-711.

Holcomb et al. (1982) Eur. J. Pharmacol. 82, 173-178.

International Preliminary Examination Report for PCT/EP 03/13111, 2004.

International Search Report for PCT/EP 03/13111, Apr. 2004.

LeWitt et al. (2005) Adjunctive Treatment of Advanced Parkinson's Disease with Rotigotine Transdermal System (PREFER Study), LeWitt 1-25.

Nair et al. (1999) Methods Find Exp. Clin. Pharmacol. Mar. 21(2), 139-151.

Ono et al. (1984) Neuropharmacol. 23(6), 637-642.

Polymeropoulos et al. (1997) Science 276, 2045-2047.

Roy & Flynn (1990) Pharaceutical Research 7(8), 842-847.

Swart et al. (1992) International J. of Pharmaceutics, 88, 165-170.

* cited by examiner

IONTOPHORETIC DELIVERY OF ROTIGOTINE FOR THE TREATMENT OF PARKINSON'S DISEASE

FIELD OF THE INVENTION

The present invention relates to an effective method for treating or alleviating symptoms of Parkinson's disease, which uses iontophoretic delivery of the dopamine receptor agonist rotigotine (INN).

TECHNICAL BACKGROUND

Parkinson's disease is believed to be primarily caused by the degeneration of dopaminergic neurons in the substantia nigra. This, in effect, results in loss of tonic dopamine secretion and dopamine-related modulation of neuronal activity in the caudate nucleus, and thus in a deficiency of dopamine in certain brain regions. The resulting imbalance of neurotransmitters acetylcholine and dopamine eventually results in disease related symptoms. Although usually regarded as a motor system disorder, Parkinson's disease is now considered to be a more complex disorder that involves both motor and non-motor systems. This debilitating disease is characterized by major clinical features including tremor, bradykinesia, rigidity, dyskinesia, gait disturbances, and speech disorders. In some patients, dementia may accompany these symptoms. Involvement of the autonomic nerve system may produce orthostatic hypotension, paroxysmal flushing, problems with thermal regulation, constipation, and loss of bladder and sphincter control. Psychological disorders such as loss of motivation and depression may also accompany Parkinson's disease.

Parkinson's disease is primarily a disease of middle age and beyond, and it affects both men and women equally. The highest rate of occurrence of Parkinson's disease is in the age group over 70 years old, where Parkinson's disease exists in 1.5 to 2.5% of that population. The mean age at onset is between 58 and 62 years of age, and most patients develop Parkinson's disease between the ages of 50 and 79. There are approximately 800,000 people in the United States alone with Parkinson's disease.

Early motor deficits of Parkinson's disease can be traced to incipient degeneration of nigral dopamine-releasing cells. This neuronal degeneration produces a defect in the dopaminergic pathway that connects the substantia nigra to the striatum. As the disease progresses, refractory motor, autonomic, and mental abnormalities may develop, which implies that there is progressive degeneration of striatal receptor mechanisms.

The clinical diagnosis of Parkinson's disease is based on the presence of characteristic physical signs. The disease is known to be gradual in onset, slowly progressive, and variable in clinical manifestation. Evidence suggests that the striatal dopamine content declines to 20% below levels found in age-matched controls before symptoms occur.

Treatment of Parkinson's disease has been attempted with, inter alia, L-dopa (levodopa), which still is the gold standard for the therapy of Parkinson's disease. Levodopa passes the blood-brain barrier as a precursor for dopamine and is then converted into dopamine in the brain. L-dopa improves the symptoms of Parkinson's disease but may cause severe side effects. Moreover, the drug tends to lose its effectiveness after the first two to three years of treatment. After five to six years, only 25% to 50% of patients maintain improvement.

Furthermore a major drawback of currently utilized therapies for Parkinson's disease is the eventual manifestation of the "fluctuation syndrome", resulting in "all-or-none" conditions characterized by alternating "on" periods of mobility with dyskinesias and "off" periods with hypokinesia or akinesia. Patients who display unpredictable or erratic "on-off" phenomena with oral anti-Parkinson therapy have a predictable beneficial response to i.v. administration of L-dopa and other dopamine agonists, suggesting that fluctuations in plasma concentrations of drug are responsible for the "on-off" phenomena. The frequency of "on-off" fluctuations has also been improved by continuous infusions of the dopamine receptor agonists apomorphine and lisuride. However, this mode of administration is inconvenient. Therefore, other modes of administration providing a more constant plasma level, such as topical administration, are beneficial and have been suggested in the past.

As mentioned above, one treatment approach for Parkinson's disease involves dopamine receptor agonists. Dopamine receptor agonists (sometimes also referred to as dopamine agonists) are substances which, while structurally different from dopamine, bind to different subtypes of dopamine receptors and trigger an effect which is comparable to that of dopamine. Due to the reduced side-effects, it is advantageous when the substances selectively bind to a sub-group of dopamine receptors, i.e. the D2 receptors.

One dopamine receptor agonist which has been used to treat the symptoms of Parkinson's disease is rotigotine. It has mostly been tested in the form of its hydrochloride. Rotigotine is the International Non-Proprietary Name (INN) of the compound (−)-5,6,7,8-tetrahydro-6-[propyl-[2-(2-thienyl)ethyl]-amino]-1-naphthalenol having the structure shown below

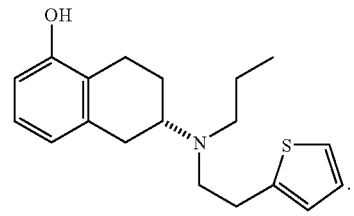

It has before been known to administrate rotigotine by passive transdermal therapeutic systems (TTS). Such passive transdermal therapeutic systems for the administration of rotigotine have been described for example in WO 94/07468 and WO 99/49852. However, the rotigotine flux obtained with these passive transdermal therapeutic systems is not necessarily sufficient for all patients.

Another dopamine agonist which has been used in the treatment of Parkinson's disease is R-apomorphine. R-apomorphine is the International Non-Proprietary Name (INN) of the compound (R)-5,6,6a,7-tetrahydro-6-methyl-4H-dibenzoquinoline-11,12-diol having the structure shown below

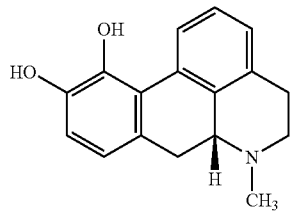

Several approaches to develop a system for iontophoretic administration of R-apomorphine have previously been described (see for example R. van der Geest, M. Danhof, H. E. Bodde "Iontophoretic Delivery of Apomorphine: In Vitro Optimization and Validation", Pharm. Res. (1997), 14, 1797-

1802; M. Danhof, R. van der Geest, T. van Laar, H. E. Boddé, "An integrated pharmacokinetic-pharmacodynamic approach to optimization of R-apomorphine delivery in Parkinson's disease", Advanced Drug Delivery Reviews (1998), 33, 253-263). However, in spite of these efforts, only concentrations at the lower end of the therapeutic concentration range of 1.4 to 10.7 ng/ml could be obtained.

A further dopamine antagonist is ropinirole hydrochloride. Ropinirole (INN) is (4-[2-dipropylamina)ethyl]-1,3-dihydro-2H-indol-2-one) having the structure shown below

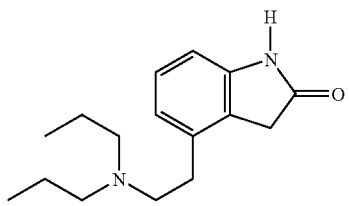

Although the iontophoretic administration of ropinirole was considered feasible, it was only possible to obtain fluxes at the lower end of the therapeutic range (see A. Luzardo-Alvarez, M. B. Delgado-Charro, J. Blanco-Méndez, "Iontophoretic Delivery of Ropinirole Hydrochloride: Effect of Current Density and Vehicle Formulation", Pharmaceutical Research (2001), 18(12), 1714-1720).

Many patients need concentrations that are significantly higher than the ones feasible using iontophoretic delivery of apomorphine or ropinirole.

In view of the broad range of symptoms of Parkinson's disease and the differing severity, there is a strong demand for a method which allows adjusting the rotigotine flux across the skin and at the same time allows for a constant receptor stimulation of the dopamine receptors of Parkinson patients. Preferably such a system should also allow for rotigotine fluxes higher than the ones achieved by passive transdermal delivery systems.

In view of the discouraging experiences with the iontophoretic delivery of apomorphine, it has been surprising that iontophoretic delivery of rotigotine could provide plasma levels of rotigotine which are not only higher than the ones of conventional passive diffusion systems but are actually in a range that allows for the delivery of pharmaceutically effective drug dosages. The results obtained by using this invention allow for a reasonable expectation that an effective treatment of Parkinson's disease can be provided. It should be understood that the term "treatment" in the context of this application is meant to designate a treatment or alleviation of the symptoms of Parkinson's disease, rather than a real causative treatment leading to a complete cure.

SUMMARY OF THE INVENTION

The present invention provides the use of a composition comprising rotigotine and at least one chloride salt in a concentration of 1 to 140 mmol/l, the composition having a pH of 4 to 6.5 for the preparation of a iontophoretic device for the treatment of Parkinson's disease.

Iontophoresis is the introduction of various ions into the skin by means of electricity. If compared to passive transdermal delivery, iontophoresis provides for several advantages which are useful in the treatment of Parkinson's disease:

it allows programming of the flux at the required therapeutic rate by adjusting the electric current, and it permits a rapid start or termination of administration of the medication, if needed, by simply turning the iontophoretic delivery system on or off.

As the iontophoretic flux is influenced by several parameters, it is crucial for achieving an optimal flux to separately optimise these parameters.

Surprisingly, it was found that using a composition having a pH of 4 to 6.5 and comprising rotigotine and at least one chloride salt in a concentration of 1 to 140 mmol/l in the donor chamber of the iontophoretic device, fluxes well within the therapeutic range could be achieved.

By reducing the electrolyte concentration in the donor compartment it was possible to achieve the target iontophoretic flux at lower current density or to increase the transdermal dose per area unit.

During the studies conducted to evaluate the feasibility of iontophoretic delivery of rotigotine, it was found that the solubility of rotigotine decreases when the pH is increased. However, surprisingly it was found that a therapeutically relevant rate was achieved within the pH interval of 4 to 6.5 at very low rotigotine concentrations.

To provide for an optimal flux across human stratum corneum it was also necessary to provide for a sufficient concentration of Cl⁻ ions for the electrode reaction in the donor phase. However, while maintaining the electrode reaction the addition of chloride salts reduces the solubility of rotigotine. Thus, a concentration of chloride salts of 1 to 140 mmol/l, preferably 50 to 100 mmol/l, more preferably 60 to 80 mmol/l, proved optimal.

The rotigotine concentration may be varied in accordance with the patient's needs and the flux required for obtaining a therapeutic effect in the treatment Parkinson's disease. However, for a optimal performance it is preferably at least 0.5 mg/ml, more preferably 0.5 mg/ml to 3 mg/ml.

All chloride salts which are pharmaceutically acceptable may be employed in the composition of the invention. In a preferred embodiment of the invention the chloride salt is selected from NaCl, triethylammonium chloride and tributylammonium chloride. Triethylammonium chloride and tributylammonium chloride are especially preferred, because they result in higher fluxes of rotigotine.

In an especially preferred embodiment of the invention the composition, which is used as the donor phase of the iontophoretic device, comprises rotigotine in a concentration of 0.5 to 3 mg/ml and at least one of triethylammonium chloride and tributylammonium chloride in a concentration of 60 to 80 mmol/l, the donor phase has a pH of 4.5 to 5.5.

In another aspect the present invention provides a method for the treatment of Parkinson's disease, wherein a iontophoretic device, which comprises a composition comprising rotigotine and at least one chloride salt in a concentration of 1 to 140 mmol/l, the composition having a pH of 4 to 6.5, is applied onto the skin of a patient in need thereof.

Any conventional iontophoretic device may be used in the invention. Such iontophoretic devices are described e.g. in V. Nair, O. Pillai, R. Poduri, R. Panchagnula, "Transdermal Iontophoresis. Part I: Basic Principles and Considerations" Methods Find. Exp. Clin. Pharmacol. (1999), 21(2), 139-151.

The current density employed during iontophoresis may be varied according to the patient's needs and will depend on the iontophoretic device and the composition used. A suitable current may be determined by the attendant physician. In general, a suitable current density will be in the range of preferably 200 to 500 µA/cm².

EXAMPLE 1

In vitro iontophoretic studies for the administration of rotigotine were carried out with three-chamber flow-through diffusion cells as described by R. van der Geest et al. (R. van der Geest, M. Danhof, H. E. Boddé, "Validation and testing of a new iontophoretic continuous flow through transport cell", J. Control. Release (1998), 51, 85-19). On both sides of the acceptor compartment human stratum corneum (SC) was situated. A dialysis membrane having a 5.000 Da cut-off was used as supporting membrane. The volume of the outer chambers was approximately 2 ml, while the volume of the acceptor compartment was 0.54 ml. The two outer chambers contained the silver plate (anode) or silver/silver chloride (cathode) driver electrons. The donor phase consisted of rotigotine solution buffered with 5 mM citrate buffer (2.1 mM sodium citrate dihydrate and 2.9 mM citric acid).

Using this set-up, a pH in the donor chamber of 5, a current density of 500 µA/cm², a pH in the acceptor chamber of 7.4, a temperature of 20° C. and an NaCl concentration in the donor chamber of 70 mmol/l, the flux of rotigotine was measured for different drug concentrations in the donor phase.

| Rotigotine conc. (mg/ml) (Donor solution) | Rotigotine conc. (mM) (Donor solution) | Flux (nmol/cm²/h) Rotigotine |
|---|---|---|
| 0.5 | 1.4 | 22.9 |
| 1.0 | 2.8 | 30.2 |
| 1.4 | 3.98 | 53.2 |

EXAMPLE 2

Using a similar procedure as in Example 1 and a concentration of rotigotine of 1.4 mg/ml (3.98 mM), a pH in the donor chamber of 5, a current density of 500 µA/cm², a pH in the acceptor chamber of 7.4 and a temperature of 20° C., but substituting triethylammonium chloride (TEACl) or tributylammonium chloride (TBACl) for NaCl, the influence of the different cations on the flux was evaluated. The concentration of the chloride salts in the donor solution was 70 mmol/l.

| Co-ions source | Flux (nmol/cm²/h) Rotigotine |
|---|---|
| NaCl | 53.2 |
| TEACl | 72.8 |
| TBACl | 62.0 |

EXAMPLE 3

Using a similar procedure and the same parameters as in Example 2, the influence of reducing the pH in the acceptor chamber from 7.4 to 6.2 was evaluated for different chloride salts. The concentration of the chloride salts in the donor solution was 70 mmol/l.

| Co-ions source | Flux (nmol/cm²/h) Rotigotine |
|---|---|
| NaCl | 58.9 |
| TEACl | 43.2 |
| TBACl | 76.5 |

The invention claimed is:

1. A method for treatment of Parkinson's disease comprising applying an iontophoretic device, which comprises a composition comprising (a) rotigotine in a concentration sufficient to provide a therapeutically effective rotigotine flux for treatment of Parkinson's disease, and (b) at least one chloride salt selected from the group consisting of triethylammonium chloride, tributylammonium chloride and combinations thereof in a concentration of 1 to 140 mmol/l, the composition having a pH of 4 to 6.5, onto skin of a patient in need thereof.

2. The method of claim 1, wherein the concentration of rotigotine in the composition is at least 0.5 mg/ml.

3. The method of claim 1, wherein the concentration of rotigotine in the composition is 0.5 to 3 mg/ml.

4. The method of claim 1, wherein the concentration of the chloride salt is 60 to 80 mmol/l.

5. The method of claim 1, wherein the composition forms a donor phase of the iontophoretic device.

6. The method of claim 5, wherein the composition forming the donor phase of the iontophoretic device comprises rotigotine in a concentration of 0.5 to 3 mg/ml and at least one of triethylanimonium chloride and tributylanimonium chloride in a concentration of 60 to 80 mmol/l, and wherein the pH of the donor phase is 4.5 to 5.5.

7. A method for treatment of Parkinson's disease comprising applying an iontophoretic device, which comprises a composition comprising (a) rotigotine in a concentration sufficient to provide a therapeutically effective rotigotine flux for treatment of Parkinson's disease, and (b) at least one pharmaceutically accentable chloride salt in a concentration of 1 to 140 mmol/l, the composition having a pH of 4 to 6.5, onto skin of a patient in need thereof.

8. The method of claim 7, wherein the concentration of rotigotine in the composition is at least 0.5 mg/ml.

9. The method of claim 7, wherein the concentration of rotigotine in the composition is 0.5 to 3 mg/ml.

10. The method of claim 7, wherein the at least one chloride salt is selected from NaCl, triethylanimonium chloride and tributylammonium chloride.

11. The method of claim 7, wherein the concentration of the chloride salt is 60 to 80 mmol/l.

12. The method of claim 7, wherein the composition forms a donor phase of the iontophoretic device.

* * * * *

UNITED STATES PATENT AND TRADEMARK OFFICE
CERTIFICATE OF CORRECTION

| | | |
|---|---|---|
| PATENT NO. | : 7,632,859 B2 | Page 1 of 1 |
| APPLICATION NO. | : 10/713424 | |
| DATED | : December 15, 2009 | |
| INVENTOR(S) | : Gai Ling Li et al. | |

It is certified that error appears in the above-identified patent and that said Letters Patent is hereby corrected as shown below:

Column 6, line 35, "triethylanimonium" should be changed to --triethylammonium-- and "tributylanimonium" should be changed to --tributylammonium--; line 43, "accentable" should be changed to --acceptable--; line 51, "triethylanimonium" should be changed to --triethylammonium--.

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,632,859 B2 | Page 1 of 1 |
| APPLICATION NO. | : 10/713424 | |
| DATED | : December 15, 2009 | |
| INVENTOR(S) | : Li et al. | |

It is certified that error appears in the above-identified patent and that said Letters Patent is hereby corrected as shown below:

On the Title Page,

Item [*] Notice: Subject to any disclaimer, the term of this patent is extended or adjusted under 35 USC 154(b) by 797 days Delete the phrase "by 797 days" and insert -- by 1,465 days --

Signed and Sealed this

Thirty-first Day of August, 2010

David J. Kappos
*Director of the United States Patent and Trademark Office*